US007544361B2

(12) United States Patent
Arakawa et al.

(10) Patent No.: US 7,544,361 B2
(45) Date of Patent: Jun. 9, 2009

(54) HETERO TYPE PENTAMER RECOMBINANT VACCINE

(75) Inventors: Takeshi Arakawa, Naha (JP); Masanao Kikukawa, Urasoe (JP); Isao Shimabukuro, Naha (JP); Masayuki Tadano, Okinawa (JP); Yasunobu Matsumoto, Tokyo (JP); Naotoshi Tsuji, Tsukuba (JP); Yoshiya Sato, Okinawa (JP)

(73) Assignees: Advanced Medical Biological Science Institute Co. Ltd., Nanjo-shi (JP); University of the Ryukyus, Nakagami-gun (JP)

( * ) Notice: Subject to any disclaimer, the term of this patent is extended or adjusted under 35 U.S.C. 154(b) by 363 days.

(21) Appl. No.: 10/565,595

(22) PCT Filed: Jul. 23, 2004

(86) PCT No.: PCT/JP2004/010459

§ 371 (c)(1),
(2), (4) Date: Jun. 29, 2006

(87) PCT Pub. No.: WO2005/010050

PCT Pub. Date: Feb. 3, 2005

(65) Prior Publication Data

US 2006/0246087 A1 Nov. 2, 2006

(30) Foreign Application Priority Data

Jul. 24, 2003 (JP) ............................ 2003-279156
Dec. 10, 2003 (JP) ............................ 2003-412053

(51) Int. Cl.
*A61K 39/385* (2006.01)
*A61K 39/12* (2006.01)
*A61K 39/295* (2006.01)
*A61K 9/28* (2006.01)
*C07K 19/00* (2006.01)
*C07K 17/00* (2006.01)
*C12N 15/62* (2006.01)
*C12N 15/63* (2006.01)
*C12N 1/21* (2006.01)

(52) U.S. Cl. .............................. 424/197.11; 424/186.1; 424/192.1; 424/193.1; 424/196.11; 424/201.1; 530/350; 536/23.1; 435/320.1; 435/252.3; 435/69.3; 435/69.7

(58) Field of Classification Search ...................... None
See application file for complete search history.

(56) References Cited

U.S. PATENT DOCUMENTS 5,589,384 A * 12/1996 Lipscombe et al. ..... 435/252.33
2008/0286297 A1* 11/2008 Florack et al. ......... 424/195.11

FOREIGN PATENT DOCUMENTS

| JP | 3-178995 | 8/1991 |
| JP | 6-206900 | 7/1994 |
| JP | 2003-116385 | 4/2003 |

OTHER PUBLICATIONS

Jobling et al (Infection and Immunity 70:1260-1271, 2002).*
Wu et al (Journal of Biological Chemistry 278: 46007-13, 2003).*
Sissela Liljeqvist, et al. "Fusions to the cholera toxin B subunit: influence on pentamerization and GM1 binding" Journal of Immunological Methods, vol. 210, No. 2, XP-004112016, Dec. 29, 1997, pp. 125-135.
Tetsuya Harakuni, et al. "Heteropentameric Cholera Toxin B Subunit Chimeric Molecules Genetically Fused to a Vaccine Antigen Induce Systemic and Mucosal Immune Responses: a Potential new Strategy To Target Recombinant Vaccine Antigens to Mucosal Immune Systems" infection and Immunity vol. 73, No. 9, XP-002461843, Sep. 2005, pp. 5654-5665.

* cited by examiner

*Primary Examiner*—Mary E Mosher
(74) *Attorney, Agent, or Firm*—Oblon, Spivak, McClelland, Maier & Neustadt, P.C.

(57) ABSTRACT

A heteropentamer composed of a fusion monomer (32) comprising a fusion protein of an antigenic amino acid sequence and an amino acid sequence of a monomer of a mucous membrane-binding protein and a nonfusion monomer (20) of an amino acid sequence of a monomer of a mucous membrane-binding protein. A homopentamer composed of a fusion monomer including a fusion protein of an antigen derived from an envelope protein of Japanese encephalitis virus and an amino acid sequence of a monomer of a mucous membrane-binding protein. These heteropentamer and the homopentamer can be used as a vaccine.

14 Claims, 7 Drawing Sheets

→ EFFECTIVE IMMUNE RESPONSE

→ NO EFFECTIVE IMMUNIZATION

INHIBITION OF FORMATION OF PENTAMER BY INTERMOLECULAR INTERACTION

ONE FUSION MONOMER × FOUR NONFUSION MONOMERS

TWO FUSION MONOMERS × THREE NONFUSION MONOMERS

THREE FUSION MONOMERS × TWO NONFUSION MONOMERS

FIG. 5

ANTI-CTB STAINING    ANTI-JEV STAINING

CTV-JE    SIZE MARKERS    CTB-JE

SEQUENCE LISTING

<160> NUMBER OF SEQ ID NOS: 9

<210> SEQ ID NO 1
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Ile Lys Leu Lys Phe Gly Val Phe Phe Thr Val Leu Leu Ser Ser
 1               5                  10                  15

Ala Tyr Ala His Gly Thr Pro Gln Asn Ile Thr Asp Leu Cys Ala Glu
             20                  25                  30

Tyr His Asn Thr Gln Ile His Thr Leu Asn Asp Lys Ile Phe Ser Tyr
             35                  40                  45

Thr Glu Ser Leu Ala Gly Lys Arg Glu Met Ala Ile Ile Thr Phe Lys
         50                  55                  60

Asn Gly Ala Thr Phe Gln Val Glu Val Pro Gly Ser Gln His Ile Asp
 65                  70                  75                  80

Ser Gln Lys Lys Ala Ile Glu Arg Met Lys Asp Thr Leu Arg Ile Ala
                 85                  90                  95

Tyr Leu Thr Glu Ala Lys Val Glu Lys Leu Cys Val Trp Asn Asn Lys
             100                 105                 110

Thr Pro His Ala Ile Ala Ala Ile Ser Met Ala Asn Gly Pro Gly Pro
             115                 120                 125

Glu Phe Thr Tyr Gly Met Cys Thr Glu Lys Phe Ser Phe Ala Lys Asn
         130                 135                 140

Pro Ala Asp Thr Gly His Gly Thr Val Val Ile Glu Leu Ser Tyr Ser
145                 150                 155                 160

Gly Ser Asp Gly Pro Cys Lys Ile Pro Ile Val Ser Val Ala Ser Leu
                 165                 170                 175

Asn Asp Met Thr Pro Val Gly Arg Leu Val Thr Val Asn Pro Phe Val
             180                 185                 190

Ala Thr Ser Ser Ala Asn Ser Lys Val Leu Val Glu Met Glu Pro Pro
         195                 200                 205

Phe Gly Asp Ser Tyr Ile Val Val Gly Arg Gly Asp Lys Gln Ile Asn
210                 215                 220

His His Trp His Lys Ala Gly Ser Thr Leu Gly Lys Ala Phe Ser Thr
225                 230                 235                 240

Thr Leu Lys Gly Ala Gln Arg Leu Ala Ala Leu Gly Asp Thr Ala Trp
             245                 250                 255

Asp Phe Gly Ser Ile Gly Gly Val Phe Asn Ser Ile Gly Lys Ala Val
             260                 265                 270

His Gln Val Phe Gly Gly Ala Phe Arg Thr Leu Phe Gly Gly Met Ser
             275                 280                 285

Trp Ile Thr Gln Gly
             290
```

<210> SEQ ID NO 2
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgattaaat taaaatttgg tgttttttt acagttttac tatcttcagc atatgcacat      60
ggaacacctc aaatattac tgatttgtgt gcagaatacc acaacacaca aatacatacg     120
ctaaatgata agatattttc gtatacagaa tctctagctg gaaaaagaga gatggctatc     180
attactttta gaatggtgc aactttcaa gtagaagtac caggtagtca acatatagat      240
tcacaaaaaa aagcgattga aggatgaag gataccctga ggattgcata tcttactgaa      300
```

```
gctaaagtcg aaaagttatg tgtatggaat aataaaacgc ctcatgcgat tgccgcaatt    360
agtatggcaa atggccccgg tccagaattc acctatggca tgtgcacaga aaaattctcc    420
ttcgcgaaaa atccggcgga cactggtcac gggacagttg tcattgaact ctcctactct    480
gggagtgatg gccctgcaa aattccgatt gtctccgttg cgagcctcaa tgacatgacc    540
cccgtcgggc ggctggtgac agtgaacccc ttcgtcgcga cttccagtgc caattcaaag    600
gtgctggtcg agatggaacc ccccttcgga gactcctaca tcgtagttgg acggggagac    660
aagcagatca accaccattg gcataaagct ggaagcacgc tgggcaaagc cttttcaaca    720
actttgaagg gagctcagag actggcagcg ttgggtgaca cagcctggga ctttggctcc    780
attggagggg tcttcaactc cataggaaaa gccgttcacc aagtgtttgg tggtgccttc    840
agaacactct tcgggggaat gtcttggatc acacaagggt ga                      882
```

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gcggaattca cctatggcat gtgcacagaa aaattctcc                            39
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gcggaattct taccttgtg tgatccaaga cat                                   33
```

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: B subunit monomer residue
<220> FEATURE:
<221> NAME/KEY: MOD_RES
<222> LOCATION: (2)..(5)
<223> OTHER INFORMATION: Any amino acid or not present
<220> FEATURE:
<221> NAME/KEY: MOD_RES
<222> LOCATION: (6)..(13)
<223> OTHER INFORMATION: This region may encompass 2 to 4
      'Gly-Pro' repeating units
<220> FEATURE:
<221> NAME/KEY: MOD_RES
<222> LOCATION: (14)..(17)
<223> OTHER INFORMATION: Any amino acid or not present
<220> FEATURE:
<221> NAME/KEY: MOD_RES
<222> LOCATION: (18)
<223> OTHER INFORMATION: Any amino acid
<220> FEATURE:
<223> OTHER INFORMATION: see specification as filed for detailed
      description of substitutions and preferred embodiments -continued

```
<400> SEQUENCE: 5

Xaa Xaa Xaa Xaa Xaa Gly Pro Gly Pro Gly Pro Gly Pro Xaa Xaa Xaa
 1               5                  10                  15

Xaa Xaa

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Pro Gly Pro
 1

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agtatggcaa at                                                           12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggccccggtc ca                                                           12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acctatggca tg                                                           12
```

HETERO TYPE PENTAMER RECOMBINANT VACCINE

CROSS-REFERENCE TO RELATED APPLICATIONS

The present application is a 35 U.S.C. § 371 National Stage patent application of International patent application PCT/JP04/10459, filed on Jul. 23, 2004, which claims priority to Japanese patent application JP 2003-279156, filed on Jul. 24, 2003, and Japanese patent application JP 2003-412053, filed on Dec. 10, 2003.

TECHNICAL FIELD

The present invention relates to heteropentameric recombinant vaccines containing fusion proteins, and more specifically, relates to enteric-coated oral vaccines. The present invention further relates to Japanese encephalitis vaccines.

BACKGROUND ART

Heretofore, most vaccines have been produced by attenuation or inactivation of viruses and bacteria. However, according to the recent development in genetic recombinant technology, the possibility of recombinant component vaccines utilizing only a gene derived from a specific pathogen is suggested. Actually, the vaccine against hepatitis B virus is produced by recombinant technology.

However, the induction of antigen-specific immune response such as production of an antibody is difficult when an antigen for component vaccine not having an affinity to mucosal tissues is directly administered to mucous membrane. Accordingly, a significant improvement in affinity of vaccine antigens for nasal or intestinal mucous membrane has been tried by fusing mucous membrane-binding proteins such as cholera toxin B subunit (CTB), which have an affinity for mucous membrane, with the vaccine antigens (for example, Japanese Unexamined Patent Application Publication No. 6-206900). However, some antigens are difficult to be produced into such fusion proteins or cannot efficiently function as a vaccine in the form of such fusion proteins.

Furthermore, no fusion protein of a digestive tract mucous membrane-binding protein and an antigen derived from Japanese encephalitis virus has been confirmed to be useful as a Japanese encephalitis vaccine component for producing an antibody.

The present invention has been completed under these circumstances, and an object is to provide a vaccine which can be produced on an industrial scale by improving the production scale and the purification efficiency. Additionally, an object of the present invention is to provide a Japanese encephalitis component vaccine.

DISCLOSURE OF INVENTION

According to the present invention, the following nucleic acid molecules (DNA and RNA), a fusion protein, a pentamer, a vaccine, and the like are provided.

[1] A heteropentamer composed of a fusion monomer including a fusion protein of an antigenic amino acid sequence and an amino acid sequence of a monomer of a mucous membrane-binding protein and a nonfusion monomer of an amino acid sequence of a monomer of a mucous membrane-binding protein.

[2] The heteropentamer of aspect [1], wherein the antigenic amino acid sequence and the amino acid sequence of the mucous membrane-binding protein are joined via a linker.

[3] The heteropentamer of aspect [1] or [2], wherein the mucous membrane-binding protein is an enterotoxin B subunit or cholera toxin B subunit.

[4] The heteropentamer of any one of aspects [1] to [3], wherein the antigenic amino acid sequence is an antigen derived from an envelope protein of Japanese encephalitis virus.

[5] A nucleic acid molecule encoding the fusion monomer and the nonfusion monomer of any one of aspects [1] to [4], or a nucleic acid molecule complementary to the sequence encoding the fusion monomer and the nonfusion monomer.

[6] A vector, which includes the nucleic acid molecule of aspect [5] and expresses the fusion monomer and the nonfusion monomer in a transformed host.

[7] A homopentamer composed of a fusion monomer including a fusion protein of an amino acid sequence of an antigen derived from an envelope protein of Japanese encephalitis virus and an amino acid sequence of a monomer of a mucous membrane-binding protein.

[8] A fusion monomer protein including an amino acid sequence of an antigen derived from an envelope protein of Japanese encephalitis virus and an amino acid sequence of a monomer of a mucous membrane-binding protein.

[9] The fusion monomer protein of aspect [10], which includes (1) the amino acid sequence of SEQ ID NO: 1; or (2) an amino acid sequence resulting from deletion, substitution, insertion, and/or addition of one or more amino acids in the above-mentioned amino acid sequence and having Japanese encephalitis virus antigenicity and a mucous membrane-binding property.

[10] A nucleic acid molecule encoding the protein of aspect [8] or [9], or a nucleic acid molecule complementary to a sequence encoding the protein.

[11] The nucleic acid molecule of aspect [10], which is defined by SEQ ID NO: 2.

[12] A vector, which includes the nucleic acid molecule of aspect [10] or [11] and expresses the fusion monomer in a transformed host.

[13] A host transformed with the vector of aspect [12].

[14] A host transformed with the vector of aspect [6] or [12].

[15] A vaccine including the heteropentamer of any one of aspects [1] to [4], the homopentamer of aspect [7], or the host of aspect [14].

[16] The vaccine of aspect [15], which is enteric-coated and can be orally administered.

[17] The vaccine of aspect [16], wherein the enteric coating includes calcium.

[18] A method for preparing a vaccine, which includes the steps of:

integrating a gene sequence encoding a fusion protein of an antigenic amino acid sequence and an amino acid sequence of a monomer of a mucous membrane-binding protein and a gene sequence encoding an amino acid sequence of a monomer of a mucous membrane-binding protein into a gene of a vector;

introducing the vector into a host for transformation;

expressing the vector to produce a heteropentamer composed of a fusion monomer of the fusion protein and a nonfusion monomer of the monomer; and purifying the heteropentamer secreted by the host in a culture solution.

[19] A method for intestinal immunization by orally administering the vaccine of any one of aspects [15] to [17] or the host of aspect [14] to a human or an animal.

[20] A medicinal composition for intestinal immunization by oral administration, which includes the vaccine of any one of aspects [15] to [17] or the host of aspect [14].

According to the present invention, there is provided a heteropentamer able to give the following effects:
(1) The molecular weight of a fusion vaccine molecule can be highly increased. It can be said that an increase in the size of an antigen to be fused diversifies the antigen.
(2) The pentamer-forming efficiency in heteropentamers can be improved.
(3) The purification of the heteropentamer can be simplified because the heteropentamers are secreted in a yeast-culturing supernatant.
(4) Since intestinal immunization by oral administration route can be performed by the host producing and holding intracellularlly the heteropentamers, the conformation for the direct immunization which is not necessary even the simplified purification described in (3) is available in some cases.

Furthermore, according to the present invention, the heteropentamer can be expressed in other expression systems, such as a plant, in addition to the yeast expression system. Thus, the heteropentamer is useful as a recombinant mucosal vaccine to animals and humans.

Additionally, the present invention can provide a Japanese encephalitis component vaccine.

BRIEF DESCRIPTION OF THE DRAWINGS

FIG. 5 is a photograph of the Western blotting in Example 1.

BEST MODE FOR CARRYING OUT THE INVENTION

Figure 1:
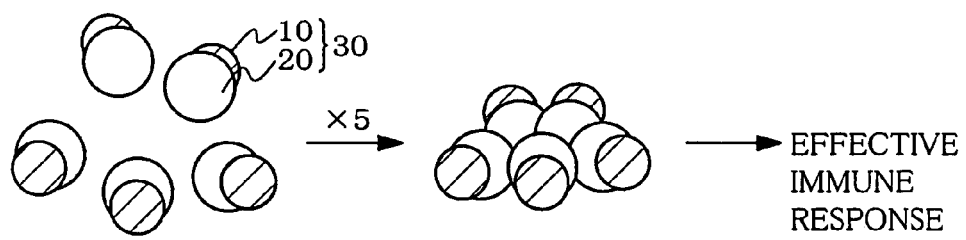
FIG. 1 is a diagram illustrating a homopentamer.

A mucous membrane-binding protein formed into a pentamer from its five monomers shows the function. In order to prepare a vaccine by gene engineering technology using a mucous membrane-binding protein, a gene sequence in which "a gene sequence of an antigen" and "a gene sequence of a single monomer of a mucous membrane-binding protein" are bound is integrated into a vector, and, as shown in FIG. 1, a host is transformed with the vector to produce fusion proteins 30 each containing the antigen 10 and the monomer 20 in the host. The fusion proteins 30 are formed into a pentamer (homopentamer) via the monomers 20 contained therein. The administration of the pentamer as a vaccine induces effective immunoreaction.

Figure 2:
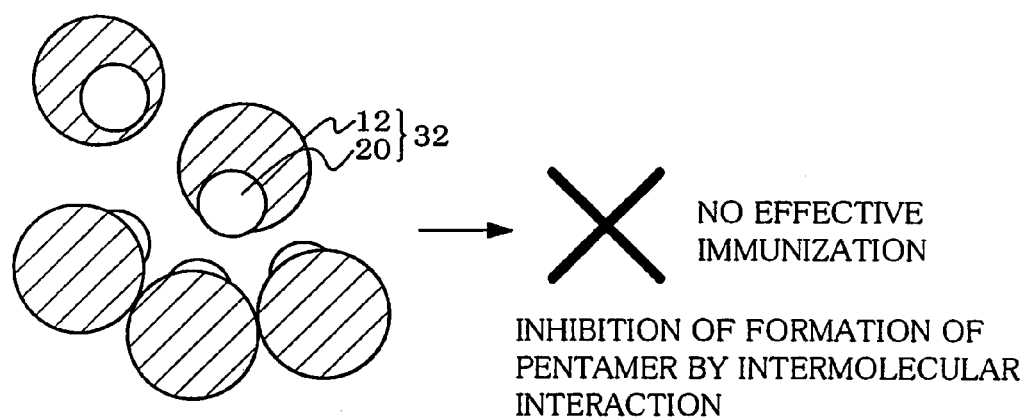
FIG. 2 is a diagram illustrating a homopentamer.

However, the present inventors have found that a method of using the mucous membrane-binding protein as a carrier of a vaccine antigen has a limitation in the molecular weight of the fusable vaccine antigen. As shown in FIG. 2, when an antigen 12 having a large molecular weight is fused with the monomer 20, the pentamer formation may be inhibited by intermolecular interaction between the fusion proteins 32. When the pentamer is not formed, the mucosal administration of such a vaccine may lead to insufficient immunization.

Furthermore, as shown in FIGS. 1 and 2, when each of the five monomers 20 of the pentamer is fused with a vaccine antigen 10 or 12, the formed pentamers are not secreted to the outside of the cell in conventional *Escherichia coli* or other expression systems and are accumulated in the cytoplasm. Consequently, the purification efficiency is low and the industrial production is difficult.

Figure 3:
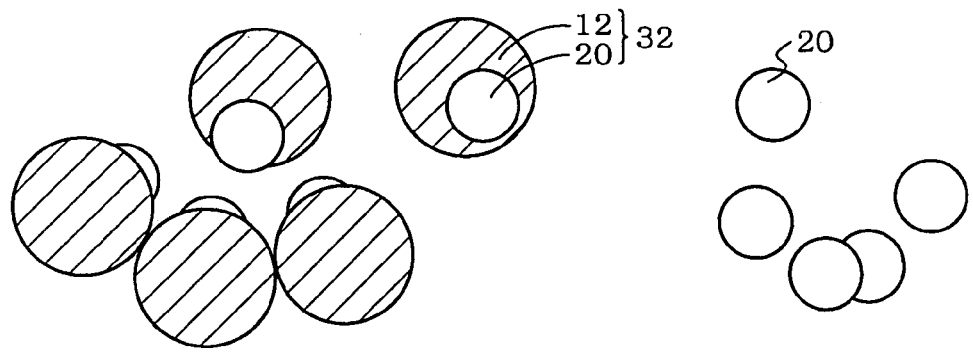
FIG. 3 is a diagram illustrating a heteropentamer.
Figure 3:
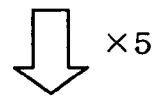
Figure 3:
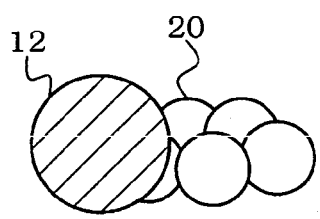
Figure 3:
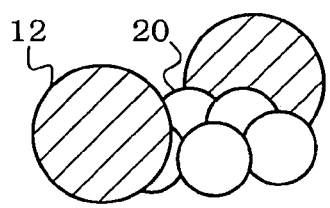
Figure 3:
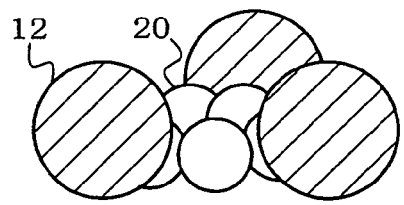

Therefore, in the present invention, "a gene sequence of a single monomer of a mucous membrane-binding protein" in addition to a gene sequence including "a gene sequence of an antigenic amino acid sequence" and "a gene sequence of a single monomer of a mucous membrane-binding protein" is integrated into a vector, and a host is transformed with the vector. These genes are coexpressed in a cell such as yeast to produce a "fusion protein (fusion monomer) 32" and a "monomer without the fusion of the antigen 12 (nonfusion monomer) 20" as shown in FIG. 3. These fusion monomer 32 and nonfusion monomer 20 together form a pentamer, but, unlikely the pentamers in FIGS. 1 and 2, the antigen 12 is not fused with all the monomers (heteropentamer). Therefore, the intermolecular interaction during the formation of the pentamer can be decreased to allow the fusion of high-molecular-weight antigens, which has been heretofore difficult.

The heteropentamer is classified into the following 6 types (I to VI) by the members of the monomer forming the pentamer.

|  | I | II | III | IV | V | VI |
|---|---|---|---|---|---|---|
| Fusion monomer | 0 | 1 | 2 | 3 | 4 | 5 |
| Nonfusion monomer | 5 | 4 | 3 | 2 | 1 | 0 |

The heteropentamer of the present invention mainly contains types of II to V, but may contain types of I and VI.

Since the heteropentamer has a compact molecular structure, not only the pentamer-forming efficiency is facilitated but also a large amount of the pentamer is secreted in the cell culture medium, e.g., in yeast culture medium. As a result, the subsequent isolation and purification of the recombinant molecules are simplified. Thus, the protein production at an industrial scale is possible. The pentamer-molecule-forming efficiency of a hetero-type fusion protein antigen is significantly facilitated compared to that of a homo-type fusion protein antigen, and the amount of the pentamer antigen having the mucosal immunogenicity is increased in the host cell. Therefore, the effect of intestinal immunization by direct oral administration of the host (plant, yeast, etc.), which carries a vaccine containing the heteropentamer in its cytoplasm, can be improved.

An exemplary fusion monomer of the present invention is a fusion monomer protein composed of an amino acid sequence of an antigen derived from Japanese encephalitis virus envelope protein and an amino acid sequence of a monomer of a mucous membrane-binding protein.

This fusion monomer protein includes, for example, the amino acid sequence represented by SEQ ID NO: 1. This fusion monomer protein can be produced, for example, by expressing in a transformed host a vector containing a nucleic acid molecule encoding the fusion monomer protein represented by SEQ ID NO: 2 or a nucleic acid molecule complementary to the sequence encoding the protein.

Functional derivatives of the above-mentioned fusion monomer protein, for example, proteins including an amino acid sequence resulting from deletion, addition, insertion, and/or substitution of one or more amino acids in the above-mentioned amino acid sequence and proteins including an amino acid sequence having at least 70%, preferably 80% or more, and more preferably 90% or more homology to the above-mentioned amino acid sequence, can be employed in the present invention provided these proteins have the characteristic functions of the proteins of the present invention. Here, the homology of the amino acid sequence can be defined as a positive percentage shown by BLASTP algorithm which is available at the Internet site http://www.ncbi.n/m.nih.gov/egi-gin/BLAST by a search using the default parameter (matrix=Blosum62; gap existence cost =11; gap extension cost=1) of the program.

The nucleic acid molecule encoding the above-mentioned protein is also useful for preparing a sensor protein of the present invention. Herein, examples of the nucleic acid molecules include those specifically shown in this specification and those encoded by other many nucleotide sequences caused by degeneracy of a genetic code. In some expression systems, codons most frequently-used in that host can be advantageously used. The nucleic acid molecules having these degenerate sequences are also included in the nucleic acid of this invention.

The heteropentamer of the present invention will now be further described in detail.

The term "mucous membrane-binding protein" used in the present invention is a protein antigen having ability to directly or indirectly bind to a mucous membrane via a receptor such as a glycolipid found in the mucous membrane. Examples of the mucous membrane include respiratory mucosal tissues of nasal cavity and respiratory tract, mucous membranes of digestive system, e.g., oral cavity, esophagus, stomach, duodenum, small intestine, colon, and rectum, and mucous membrane of genitalia, e.g., vagina. The representative examples are cholera toxin (CT) and heat-labile toxin (LT). These CT and LT are very closely related proteins produced by *Vibrio cholerae* and enterotoxigenic *E. coli* (ETEC), respectively. These toxins each are composed of an A subunit responsible for toxicity and a non-toxic B subunit (CTB and LTB), and entry of the A subunit into the cell is facilitated by the B subunit. This B subunit binds to GM1-monosialogangioside receptor. GM1 is present on the surface of a variety of mammalian tissues, including mucosal epithelium. When these mucous membrane-binding proteins are orally or intranasally administered with an antigen, immune response against the antigen is induced by the GM1 binding properties of the B subunits.

The term "antigenic amino acid sequence" of the present invention includes antigens derived from pathogens such as viruses, bacteria, and parasites, in particular, amino acid sequences having an epitope which is important for infection protection in humans and animals. Autoantigens, which are important for autoimmune diseases of humans and animals, are also included. Furthermore, prion proteins, which are infectious forms of auto- or analogous antigens by degeneration thereof, are included. Additionally, proteins containing allergens, which are a factor of allergic reactions, are also included. Examples of the pathogens preferably include arthropod-borne pathogens such as Japanese encephalitis virus and malaria and enteric parasites such as swine *ascaris*. Examples of the autoimmune diseases include insulin dependent diabetes and inflammatory rheumatism. Examples of prion diseases include Creutzfeldt-Jakob disease. Examples of allergens include antigens inducing food allergy, mite allergens, and allergens for pollen allergy triggered by Japan cedar.

The term "antigenic amino acid sequence" used in the present invention can induce both positive and negative immune responses, for example, positive response to activate humoral immunity (antibody response) or cellular immunity and negative response (immune tolerance) to suppress inflammatory reactions which are caused in specific or non-specific tissues or organs.

Examples of the epitope may be derived from a virus, bacterium, fungus, yeast, or parasite.

The length of the "antigenic amino acid sequence" does not have any limitation. However, the sequence should not disrupt the ability of the heteropentamer to bind to GM1-ganglioside. The sequence may be up to 200 residues, up to 150 residues, or up to 100 residues long. Additionally, a shorter sequence of up to 60, for example up to 30 or 20, amino acid residues in length may be employed.

The fusion proteins constituting the fusion monomers of the present invention have a monomer protein (12 kDa) at the N-terminus and an arbitrary antigen protein (up to 22 kDa) at the C-terminus.

A linker may be provided between the "amino acid sequence of antigenic epitope" and the "amino acid sequence of the monomer of a mucous-binding protein". The linker has a four to twenty-amino acid sequence of a repeat sequence of Gly-Pro. There may be up to four residues of the repeat sequence, for example. The linker is fused to the C-terminus of the monomer.

The Gly-Pro repeat sequence may be adjacent by other amino acid residues. These are suitably uncharged non-aromatic residues. Up to four amino acid residues, for example two amino acid residues or one amino acid residue, may be provided after the B subunit monomer residue and before the Gly-Pro repeat sequence. Up to four amino acid residues, for example two amino acid residues or one amino acid residue, may be provided after the Gly-Pro repeat sequence and before the amino acid sequence of a pathogen epitope.

The amino acid sequence of the epitope may be fused to the C-terminus of the linker.

The fusion monomer can be represented by the formula (SEQ ID NO: 5) (I):

X—Y1-(Gly-Pro)n-Y2-Z    (I)

in which X represents the B subunit monomer residue, Y1 and Y2 are each independently peptide bonds or amino acid sequences of up to 4 amino acid residues, Z represents the amino acid sequence of the epitope, and n is 2, 3, or 4. Preferably, Y1 is leucine (L), and Y2 denotes the amino acid residues glutamic acid-isoleucine (EI).

The "gene sequence of the fusion monomer" and the "gene sequence of the nonfusion monomer" preferably exist in parallel on a plasmid vector, and, depending on the gene transferring method, exist in the ring structure (plasmid) in the cytoplasm or are inserted in chromosome in the nucleus or chloroplast after linearization. The "gene sequence of the fusion monomer" and the "gene sequence of the nonfusion monomer" may form an expression unit including the respective own promoter/terminator sequences transcribed in a monocistronic fashion of a eukaryote; may hold a ribosome-binding sequence such as IRES, which is important for expression of a plurality of genes, therebetween; or may form operon in a polycistronic fashion expression manner of a prokaryote. A plurality of copies of each of the "gene sequence of the fusion monomer" and the "gene sequence of the nonfusion monomer" may exist in the host cell, and the ratio between them may not be necessarily 1:1.

The fusion monomers and the nonfusion monomers are correctly folded and assembled into pentamers. The heteropentamer can bind to GM1-ganglioside and, at the same time, provides an amino acid sequence having immunogenicity. Therefore, the heteropentamer can be used as a vaccine, in particular, as a mucosal (intranasal, oral, etc.) vaccine.

The heteropentamer includes an amino acid sequence functional as an enterotoxin B subunit which is capable of ADP-ribosylating GTPase, and can bind to GM1-ganglioside.

The heteropentamer may be composed of LTB or CTB. Actually, the natural B subunit amino acid sequence, LTB and CTB may be modified by substitution, insertion, or deletion of one or more amino acids in the range that the antibody prepared against the natural B subunit can bind to the fusion protein of the modified subunit amino acid sequence.

Such a modified amino acid sequence may be employed provided the monomer including the modified amino acid sequence retains abilities to form pentamers and to bind to GM1-ganglioside. The physicochemical characters of the original sequence should be preserved, i.e., in terms of charge density, hydrophilicity/hydrophobicity, size, and configuration. Candidate substitutions include, based on the one-letter code (Eur. J. Biochem. 138, 9-7, 1984), a substitution of G by A and vice versa; a substitution of V by A, L, or G; a substitution of K by R; a substitution of T by S and vice versa, a substitution of E by D and vice versa; and a substitution of Q by N and vice versa.

The degree of homology between the natural sequence of an enterotoxin B subunit and a modified amino acid sequence may be 80% or more, for example, 90% or more or 95% or more. The natural amino acid sequence of a B subunit may be shortened, for example, by up to 4 or up to 2 amino acid residues, at either or each terminus. Namely, the C-terminus of LTB or CTB may be shortened in this way.

The heteropentamer of the present invention can be prepared by recombinant DNA technology. Namely, the heteropentamer can be prepared by transforming a host with a vector capable of expressing the fusion and nonfusion monomers in that host, expressing the vector in the host, and isolating the produced heteropentamer.

Therefore, the preparation of the heteropentamer depends on the provision of a DNA sequence encoding the fusion and nonfusion monomers. The DNA sequence may be provided at its 5'-end with a sequence encoding a leader peptide for the fusion and nonfusion monomers so that the fusion and nonfusion monomers are released from the cytoplasm of the host cell in which they are expressed. Any appropriate leader sequence may be employed. However, typically, a DNA encoding the natural leader sequence for the B subunit is provided immediately upstream of the DNA encoding the amino acid sequence of the mature B subunit residues.

The choice of codons specifying the residues of the linker is important. Suitably, at least half of the codons are rare codons for amino acid residues in the host in which a fusion protein is expressed. Therefore, the codons should not be the optimal codons, i.e., the codons of first choice, for use in the host. Generally, they should not be the codons of second choice. At least 75%, at least 95%, or all of the codons for the linker may be rare codons. Such rare codons for *E. coli* are reported by Sharp & Li (1986). Rare codons create pauses during translation, which allows the B subunit to be correctly folded independently of the linker and fusion of the linker.

Thus, a DNA sequence encoding the desired fusion and nonfusion monomers can be obtained. The DNA sequence is inserted into a vector to prepare an expression vector expressing the fusion and nonfusion monomers when it is provided in a suitable host. Appropriate transcriptional and translational control elements are provided for the DNA sequence, in particular, a promoter and a translational termination codon are provided for the DNA sequence. The DNA sequence is located between the translation start and stop signals in the vector. The DNA sequence is provided in the correct frame such as to enable expression of the fusion and nonfusion monomers to occur in a host compatible with the vector.

The vector for use in the present invention is a gene expression vector encoding the base sequences of the fusion monomer and the nonfusion monomer and preferably including host-specific promoter/terminator base sequences which can be expressed in *E. coli*, a gram-positive bacterium, *lactobacillus*, yeast, a mammal cell, an insect cell, or a plant cell.

The coding sequence for the linker is selected so that it ends with a restriction site into which a gene encoding an antigenic amino acid sequence can be inserted. The restriction site allows the gene to be inserted in the correct reading frame. Namely, the protein translated from the gene sequence for the fusion monomer should be a fusion protein having a primary structure of a full-length.

When the B subunit is LTB, a vector capable of expressing LTB can be obtained by first cloning the LTB gene (Dallas, 1983) into the vector under the control of appropriate transcriptional and translational regulatory elements. Oligonucleotides corresponding to the linker can be synthesized and fitted to the 3'-end of the LTB gene. In particular, a DNA sequence encoding the linker can be cloned into the SpeI site located at the natural termination codon of the 3'-end of the LTB gene. A gene encoding the amino acid sequence having biological activity can be cloned in phase into an appropriately located restriction site at the 3'-end of the DNA sequence encoding the linker.

The fusion and nonfusion monomers are expressed by culturing a host transformed with the vector. The fusion and nonfusion monomers are self-assembled into a pentamer. Any appropriate host-vector system may be employed. The host may be a prokaryotic or eukaryotic host. Preferable examples of the host include *E. coli*, gram-positive bacteria, *lactobacillus*, yeast, insect cells, mammalian cells, plant cells, transgenic animal cells, and transgenic plant cells. Additionally, the "host" is not necessarily a cell. Cell-free expression systems may be employed, provided that appropriate translation and subsequent modification (glycosylation, phosphorylation, etc.) of the protein are performed.

The vector may be a plasmid. In such a case, a bacterial or yeast host, for example, gram-negative *bacillus* such as *E. coli* or *Vibrio* species, or *S. cerevisiae*, can be used. Alternatively, the vector may be a viral vector. This may be used to transfect cells of mammalian cell line, for example, Chinese hamster ovary (CHO) cells or COS cells, to cause expression.

The expressed heteropentamer can be isolated. In the present invention, since all the five monomers for forming the pentamer are not necessarily fused with an antigen, the heteropentamer is secreted from the cytoplasm to the culture medium. The heteropentamer can be isolated and purified from the culture medium. Additionally, the direct oral administration of the host itself can induce the intestinal immunization.

The purified heteropentamer, a killed vaccine of toxin-producing *E. coli* strain expressing the heteropentamer, and an attenuated live virus vaccine capable of expressing the heteropentamer can be each used as a vaccine. Typically, the vaccine includes a physiologically acceptable carrier or diluent. Conventional formulations, carriers, and diluents can be employed.

A suitable attenuated live virus vaccine may be an attenuated microorganism having a non-reverting mutation in each of two discrete genes in its aromatic biosynthetic pathway. Such microorganisms are disclosed in EP-A-0322237. The microorganism is typically a pathogenic bacterium from the genus *Salmonella* such as *S. typhi*, *S. typhimurium*, *S. dublin*, and *S. cholerasius*.

The non-reverting mutation may be generally induced in any two of aroA, aroB, aroC, aroD, and aroE genes. Preferably, one of the non-reverting mutations is in the aroA gene. A suitable attenuated microorganism harbors an expression cassette encoding the fusion and nonfusion monomers such that the fusion and nonfusion monomers can be expressed by the microorganism. For reliable expression through generations of the microorganism, the expression cassette should be stably inherited in the absence of antibiotic selection.

The vaccine can be administered by any arbitrary route. The choice of the route (for example, an oral route, an intranasal route, a respiratory tract route, a vagina route, a rectum route, and a non mucosal route such as subcutaneous, intravenous, and intramuscular administration), the dose, and the frequency of vaccination depend on the purpose of the vaccination, whether a human or animal is being treated, and the condition of the human or animal to be vaccinated.

However, typically, the heteropentamer is administered in an amount of 1 to 1000 μg per dose, preferably 10 to 100 μg per dose, by the oral, intranasal, or parenteral route. On the other hand, in the case of the attenuated S. typhi, a dose of 109 to 1011 S. typhi organisms per dose is generally convenient for a 70 kg adult patient, via the typical oral route.

The heteropentamer may be formulated for administration as a pharmaceutical composition containing a pharmaceutically acceptable carrier or diluent. Arbitrary conventional carriers and diluents can be employed.

The vaccine according to the present invention is preferably enteric-coated for oral administration. The enteric coating can prevent the vaccine from the decomposition by digestive fluids so that the vaccine reaches the intestine to be absorbed.

Any conventional enteric coating can be used, but those containing calcium are preferable from the viewpoint of cost and safety. In a method for enteric coating with calcium fine particles, as disclosed in Japanese Unexamined Patent Application Publication Nos. 7-328416, 10-5577, and 10-155876, calcium fine particles are absorbed on the surface of an oil droplet to form a shell, and then the oil droplet in the shell is substituted by a vaccine.

The oral vaccination according to the present invention can induce immunization by orally administering a vaccine containing the above-mentioned heteropentamer or a recombinant host (plant, yeast, etc.) retaining the heteropentamer in its cytoplasm directly.

The vaccine according to the present invention can be applied as a mucosal vaccine to commercial animals such as domestic animals and animals such as pets. In particular, the vaccine can be applied to humans by combination with technology encapsulating the vaccine into an enteric-coating agent. Furthermore, there is a possibility of a plant vaccine using a genetically engineered crop containing a fused gene for the heteropentamer.

Additionally, the present invention provides a homopentameric Japanese encephalitis component vaccine. Its preparation method and utilization method as a vaccine are the same as those in the above-mentioned heteropentamer except that, in the preparation method, only a DNA encoding a fusion protein of an antigen derived from Japanese encephalitis virus envelope protein and a monomer of a mucous membrane-binding protein is inserted into a vector. A host to which such a vector is introduced expresses only the fusion protein to form a homopentamer.

Japanese encephalitis virus envelope protein is used as an antigen in the following Examples, but the present invention is not limited to this and can be applied to other antigens.

EXAMPLE 1

[Preparation of Heteropentamer]

5'-end primer (SEQ ID NO: 3) and 3'-end primer (SEQ ID NO: 4) of JEV EIII were produced, and PCR was carried out using a DNA derived from Japanese encephalitis virus cell line (JaOH0566 strain) as a template. The PCR amplification product was digested by EcoRI (G/AATTC), and purified.

A DNA of CTB was inserted into a yeast expression vector pAO815 (MultiCopy Pichia Expression kit: Invitrogen), and the resulting vector was treated with EcoRI as in the PCR amplification product.

The JEV DNA treated with EcoRI was inserted into the yeast expression vector pAO815-CTB containing the CTB gene so that the fusion gene is provided in a correct frame.

A sequence encoding a hinge region was inserted downstream of the CTB gene. A sequence GPGP (SEQ ID NO: 6) between CTB and JEV EIII in the fusion protein can reduce the intermolecular interaction between both protein portions. This effectively functions for forming a pentamer of CTB. Thus, the fusion protein is formed into a pentamer and acquires a GM1-ganglioside-binding property. Since glycine (G) has the smallest side chain (H) in 20 different amino acids and proline (P) has the amino group and the carboxyl group at a right angle, they are suitable as the hinge.

E. coli XL-1 Blue strain was transformed by electroporation using a plasmid DNA, and ampicillin-resistant strain was selected with LB-Amp medium. A plasmid vector was isolated from the ampicillin-resistant strain, and DNA sequencing was carried out using a DNA sequencer (AGT ATG GCA AAT (SEQ ID NO: 7)-[CTB]-GGC CCC GGT CCA (SEQ ID NO: 8)-[GPGP (SEQ ID NO: 6) (linker)]-GAA TTC-[EcoRI]-ACC TAT GGC ATG (SEQ ID NO: 9)-[JEV EIII domain N'-terminal sequence]). The DNA base sequence is shown by SEQ ID NO: 2, and the amino acid sequence induced from the nucleotide sequence is shown by SEQ ID NO: 1. In SEQ ID NO: 2, the 1st to 372nd base sequence is derived from CTB, the 373rd to 384th base sequence is the linker, the 385th to 390th base sequence is EcoRI site, and the 391st to 882nd base sequence is JEV EIII domain N'-terminal sequence.

The produced plasmid vector pAO815-CTB:JEV EIII was digested by BamHI (G/GATCC), treated with calf intestinal alkaline phosphatase (CIAP), and then purified.

At the same time, a plasmid vector pAO815-CTB was digested by BamHI/BglII, and then subjected to agarose gel electrophoresis, and a band of a DNA fragment containing a CTB expression cassette was purified from the gel.

The above-mentioned CIAP-treated plasmid vector pAO815-CTB:JEV EIII and the DNA fragment containing the CTB expression cassette (BamHI-BglII fragment were ligated using T4 DNA ligase.

Again, E. coli XL-1-Blue strain was transformed. Plasmid vector pAO815-CTB:JEV EIII/CTB was purified from the recombinant E. coli and was cut with SalI in order to introduce the gene into yeast (Pichia pastoris GS115 strain). After the purification, electroporation was conducted at 1.5 kV. The yeast was incubated in an MD medium containing 1 M sorbitol at 28° C. for 2 to 3 days. After the incubation, in order to confirm the expression in a colony of the yeast, the yeast was incubated in BMMG medium at 30° C. at 250 rpm for 16 to 24 hr and then was transferred to BMMY medium to incubate at 30° C. at 250 rpm for 72 hr with addition of 1% methanol every 24 hours. After the 72-hour incubation, the supernatant was separated from the cells by centrifugation at 3000 rpm for 10 min.

[Immunogenicity of Heteropentamer]

(ELISA Analysis)

Figure 4:
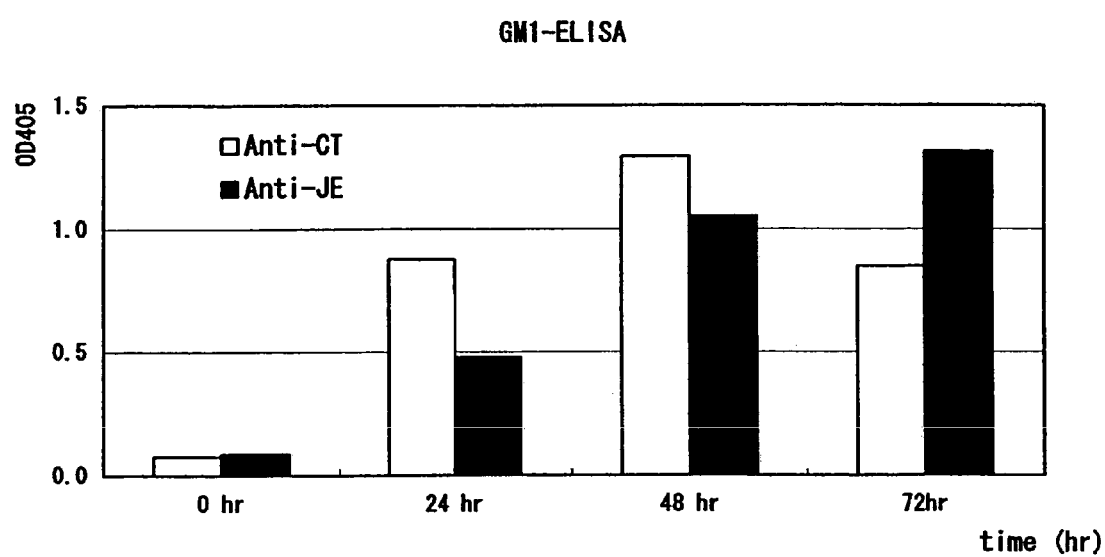
FIG. 4 is a graph showing the ELISA data in Example 1.

The resulting supernatant was analyzed by ELISA. Wells were coated with GM1-ganglioside (100 μl/well) overnight at 4° C. After washing, the wells were blocked (1 hr) with 1% BSA-PBS. The culture supernatant was applied to the wells. After washing, primary antibody (anti-JEV antibody or anti-CT antibody, 1/1000 dilution) was applied to the wells and incubated for 1 hr and then secondary antibody (anti-rabbit IgG antibody-AP conjugate: Sigma, 1/2000 dilution) was applied to the wells and incubated for 1 hr. After washing, color reaction (OD at 415 nm) was conducted. With the data shown in FIG. 4, antigens which react with anti-JEV antibody and anti-CT antibody were confirmed.

(Western Blotting Method)

Additionally, the supernatant was analyzed by Western blotting. The supernatant was applied to electrophoresis (SDS-PAGE) using acrylamide gel (gel concentration: 12.5%) at 20 mA (constant current) for 60 min and transferred on a nitrocellulose membrane at 100 V (constant voltage) for 120 min by using a wet-type transfer system.

After blocking with 5% skim milk/PBS-T at 25° C. for 60 min, the membrane was incubated with primary antibody (anti-CT antibody or anti-JEV antibody, 1/1000 dilution) at 25° C. for 60 min and then washed. Then, the membrane was incubated with secondary antibody (anti-rabbit IgG antibody, 1/1000 dilution) at 25° C. for 60 min and then washed. Then, DAB coloring was performed. A fusion protein which reacts with anti-JEV antibody and anti-CT antibody was confirmed. FIG. 5 shows the photographs of the Western blotting.

EXAMPLE 2

CTB-JEV fusion protein (homopentamer) was expressed in E. coli as in Example 1 except that only a DNA including JEV and CTB base sequences was inserted into the vector.

E. coli expressing the CTB-JEV fusion protein was disrupted to retrieve the CTB-JE fusion protein, and the fusion protein was column purified.

Figure 6:
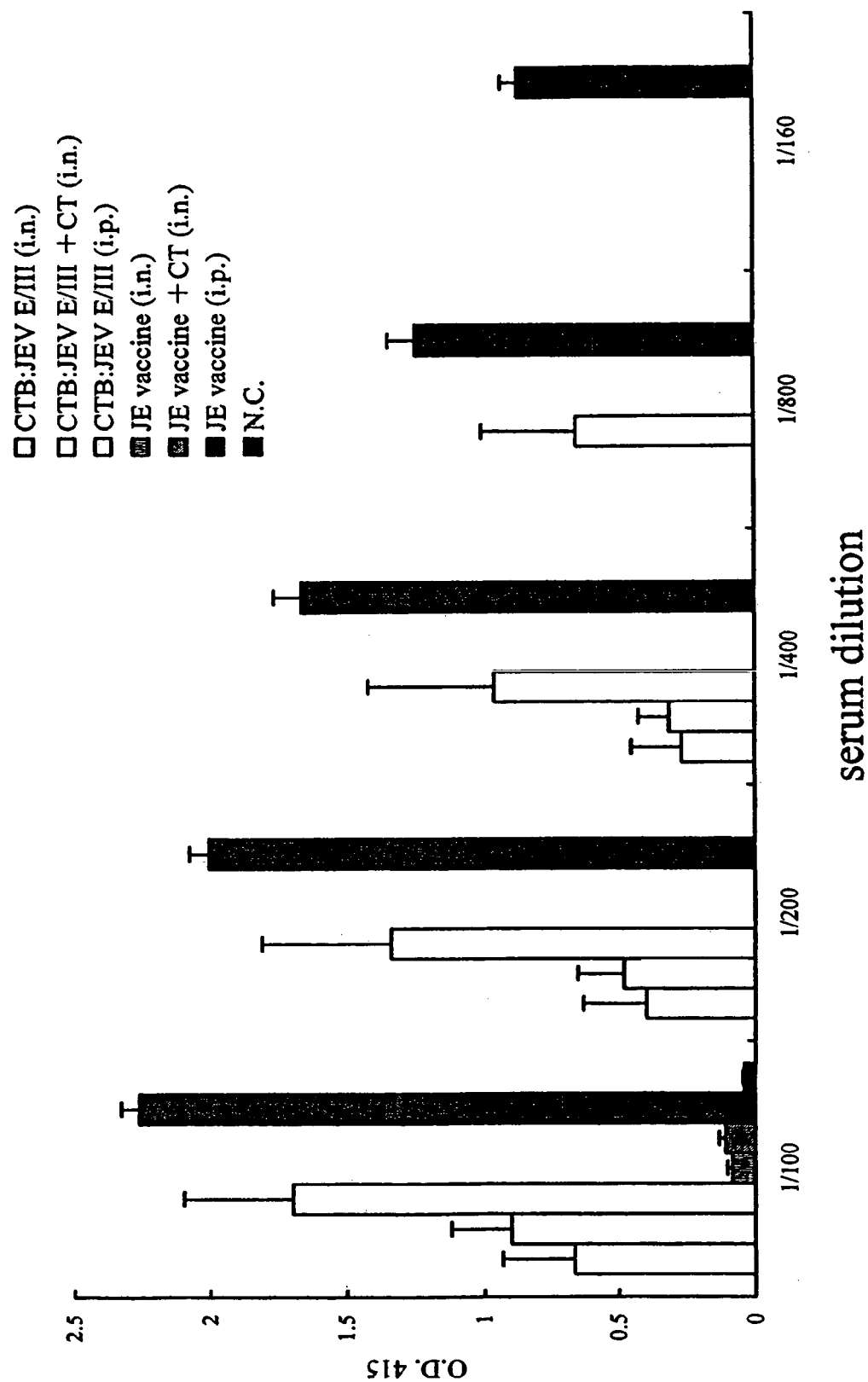
FIG. 6 is a graph showing the measurement results of JEV-specific serum IgG levels in Example 2.

The purified E. coli (CTB-JEV fusion protein), JEV vaccine, a mixture of the purified E. coli and CTB, and a mixture of JEV vaccine and CTB were intranasally (i.n.) or intraperitoneally (i.p.) administered to mice (dose: 18 µg/mouse, administration: 4 times, each group: 4 mice). The results were compared with those of non-treated mice as a negative control (NC). Blood samples were measured for JEV-specific serum IgG levels by ELISA. FIG. 6 shows the results.

With FIG. 6, it was confirmed that antibodies against JEV were induced in the blood.

Figure 7:
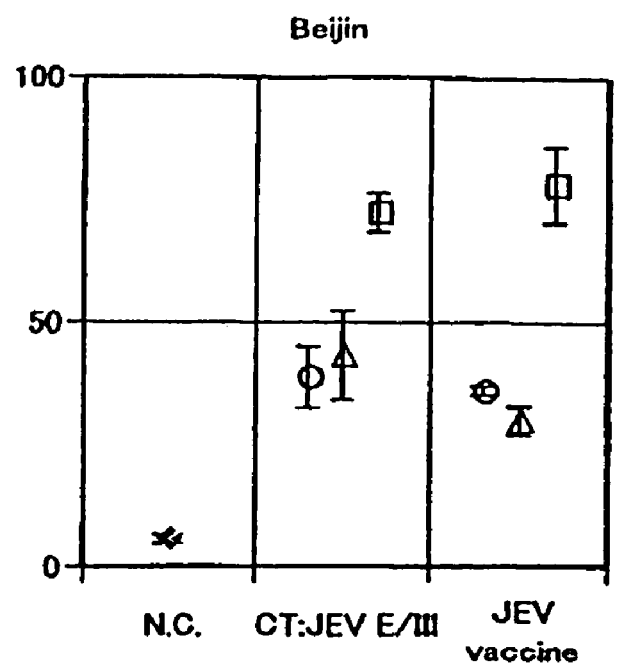
FIG. 7 is graphs showing the measurement results of neutralizing antibody titers in Example 2.
Figure 7:
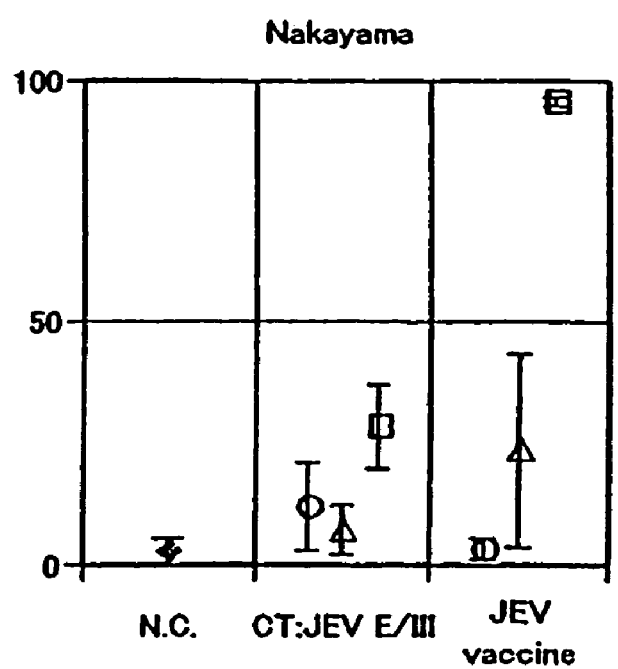

Furthermore, the neutralizing antibody titers were measured by a neutralization test. FIG. 7 shows the results. The correspondence between FIG. 7 and FIG. 6 is as follows:

○ in CT:JEV E/III of FIG. 7: CTB:JEV E•III (i.n.) in FIG. 6,

Δ in CT:JEV E/III of FIG. 7: CTB:JEV E•III+CT (i.n.) in FIG. 6,

☐ in CT:JEV E/III of FIG. 7: CTB:JEV E•III (i.p.) in FIG. 6,

○ in JEV vaccine of FIG. 7: JEV vaccine (i.n.) in FIG. 6,

Δ in JEV vaccine of FIG. 7: JEV vaccine+CT (i.n.) in FIG. 6, and

☐ in JEV vaccine of FIG. 7: JEV vaccine (i.p.) in FIG. 6.

With FIG. 7, it was confirmed that neutralizing antibodies against JEV were induced.

EXAMPLE 3

CTB-JEV fusion protein (homopentamer) was expressed in Agrobacterium as in Example 1 except that only a DNA including JEV and CTB base sequences was inserted into the vector.

Agrobacterium expressing the CTB-JEV fusion protein was intranasally or orally administered to mice (dose: intranasal administration: 0.1 g/mouse, oral administration: 1 g/mouse; administration: 3 times; each group: 5 mice). The production of anti-JEV antibodies was confirmed by ELISA. Table 1 shows the results. Mice not administered with the Agrobacterium were employed as a control.

TABLE 1

| Immunization method | | Number of positive/total mice (mean OD value) | |
|---|---|---|---|
| Dose ratio | Administration route | CTB: JEV EIII | Control |
| 1 | Intranasal | 5/5 (0.486) | 0/5 (0.069) |
| 10 | Oral | 5/5 (0.465) | 0/5 (0.024) |

With Table 1, it was confirmed that antibodies against JEV were induced by the administration via nasal and intestinal mucous membranes.

REFERENCE EXAMPLE 1

As in Example 1, a DNA including CTB base sequence was inserted into yeast expression vector pAO815, followed by expression of CTB.

Figure 8:
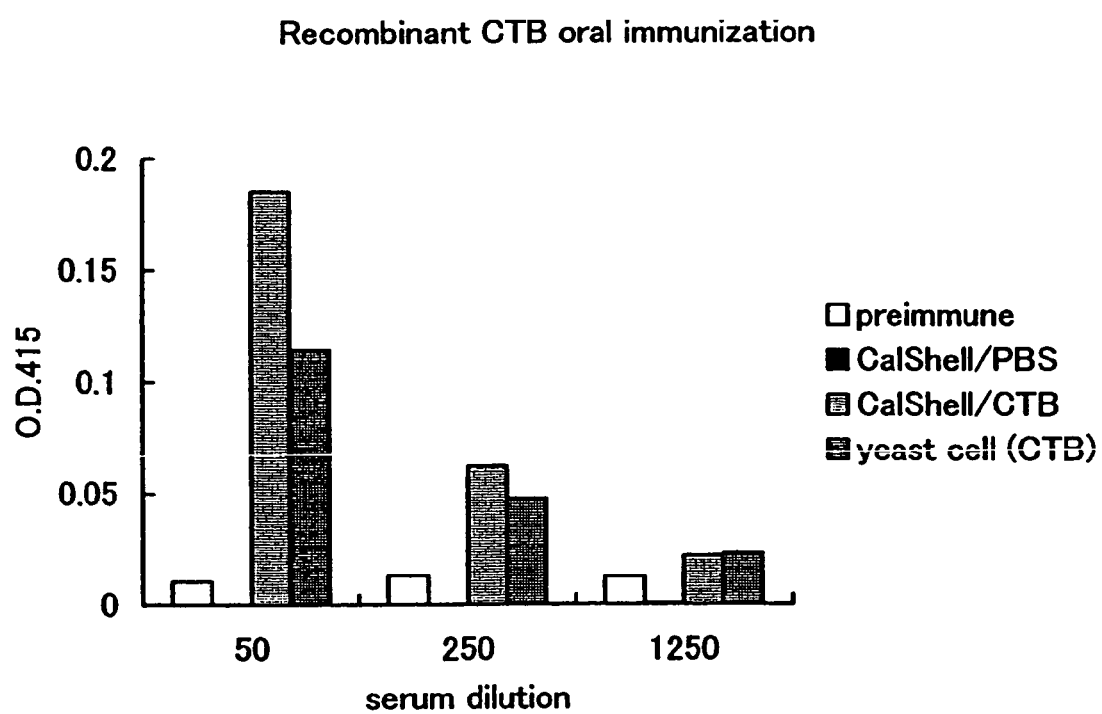
FIG. 8 is a graph showing the measurement results of CTB-specific serum IgG levels in Reference Example 1.

CTB was roughly purified from the yeast culture supernatant in which CTB was secreted, and was encapsulated with calcium to form enteric coating (CalShell/CTB). As a comparison, a phosphate buffer solution was similarly encapsulated with calcium to form enteric coating (CalShell/PBS). These enteric-coated products and recombinant yeast were orally administered to mice (dose: each enteric-coated product: 0.5 g/mouse, yeast: 0.5 g/mouse; administration: 5 times; each group: 4 mice). Blood samples before and after immunization were measured for CTB-specific serum IgG levels by ELISA. FIG. 8 shows the results.

With FIG. 8, it was confirmed that antibodies against CTB were induced in the blood.

INDUSTRIAL APPLICABILITY

The heteropentamer and the homopentamer according to the present invention are useful as a vaccine for humans or animals.

The invention claimed is:

1. A heteropentamer composed of a fusion monomer comprising a fusion protein of an antigenic amino acid sequence and the amino acid sequence of a monomer of a pentameric mucous membrane-binding protein and a nonfusion monomer of the amino acid sequence of a monomer of the mucous membrane-binding protein.

2. The heteropentamer according to claim 1, wherein the antigenic amino acid sequence and the amino acid sequence of the mucous membrane-binding protein are joined via a linker.

3. The heteropentamer according to claim 1, wherein the mucous membrane-binding protein is an enterotoxin B subunit or cholera toxin B subunit.

4. The heteropentamer according to claim 1, wherein the antigenic amino acid sequence is an antigen derived from an envelope protein of Japanese encephalitis virus.

5. A nucleic acid molecule encoding the fusion monomer and the nonfusion monomer of any one of claims 1 to 4, or a nucleic acid molecule complementary to the sequence encoding the fusion monomer and the nonfusion monomer.

6. A vector, which comprises the nucleic acid molecule of claim 5 and expresses the fusion monomer and the nonfusion monomer in a transformed host.

7. The heteropentamer of claim 4, in which the fusion monomer comprises (1) the amino acid sequence of SEQ ID NO: 1; or (2) an amino acid sequence 90 % homologous to SEQ ID NO: 1 and having Japanese encephalitis virus antigenicity and a mucous membrane-binding property.

8. The nucleic acid molecule of claim 5, wherein the nucleic acid encoding the fusion monomer comprises SEQ ID NO: 2.

9. A nonhuman host transformed with the vector of claim 6.

10. An immunogenic composition comprising the heteropentamer of any one of claims 1 to 4, or the host of claim 9.

11. The immunogenic composition of claim 10, which is enteric-coated and can be orally administered.

12. The immunogenic composition according to claim 11, wherein the enteric coating comprises calcium.

13. A method for preparing a immunogenic composition, which comprises the steps of:

integrating a gene sequence encoding a fusion protein of an antigenic amino acid sequence and an amino acid sequence of a monomer of a mucous membrane-binding protein, and a gene sequence encoding an amino acid sequence of a monomer of a mucous membrane-binding protein into a gene of a vector;

introducing the vector into a host for transformation;

expressing the vector to produce a heteropentamer composed of a fusion monomer of the fusion protein and a nonfusion monomer of the monomer; and purifying the heteropentamer secreted in a culture solution by the host.

14. A method for intestinal immunization by orally administering the immunogenic composition of claim 10 to a human or an animal.

* * * * *